United States Patent
Matsutani

(10) Patent No.: US 6,361,316 B1
(45) Date of Patent: Mar. 26, 2002

(54) DENTAL INSTRUMENT SUPPORT MECHANISM

(75) Inventor: Kanji Matsutani, Takanezawa-machi (JP)

(73) Assignee: Mani, Inc., Tochigi (JP)

(*) Notice: Subject to any disclaimer, the term of this patent is extended or adjusted under 35 U.S.C. 154(b) by 0 days.

(21) Appl. No.: 09/649,481

(22) Filed: Aug. 28, 2000

(30) Foreign Application Priority Data

Aug. 30, 1999 (JP) .................................. 11-243116

(51) Int. Cl.⁷ .................................................. A61C 1/02
(52) U.S. Cl. ........................................................ 433/108
(58) Field of Search ........................... 433/75, 76, 108, 433/109, 29, 31, 33, 94, 140

(56) References Cited

U.S. PATENT DOCUMENTS

| | | | | |
|---|---|---|---|---|
| 569,210 A | * | 10/1896 | Land | 433/75 |
| 2,233,722 A | * | 3/1941 | Weigele | 433/76 |
| 2,958,130 A | * | 11/1960 | White | 433/136 |
| 3,226,828 A | * | 1/1966 | Spalten | 433/76 |
| 4,455,137 A | | 6/1984 | Diamond | |
| 4,474,500 A | | 10/1984 | Lynch | |
| 4,573,918 A | | 3/1986 | Bareth | |
| 4,923,399 A | | 5/1990 | Funderburg, Jr. | |
| 5,312,250 A | | 5/1994 | Ellman et al. | |
| 5,575,646 A | * | 11/1996 | Giannella | 433/76 |
| 5,743,734 A | | 4/1998 | Heath et al. | |

* cited by examiner

Primary Examiner—Cary E. O'Connor
(74) Attorney, Agent, or Firm—Muramatsu & Associates

(57) ABSTRACT

A dental instrument support mechanism for establishing stable support for dental instruments such as a dental cutting tool, a drill, a fiber scope and the like. The dental instrument support mechanism is formed with a base portion, and a support arm connected to the base portion at one end for holding a dental instrument at another end. The dental instrument held by the support arm is fixedly maintained a positional relationship with a dental object in an oral cavity of a patient. The dental instrument support mechanism is attached to one of a head, face, jaw, tooth of the patient or a treatment bed.

13 Claims, 3 Drawing Sheets

DENTAL INSTRUMENT SUPPORT MECHANISM

FIELD OF THE INVENTION

This invention relates to a support mechanism for supporting dental instruments, and more particularly, to a dental instrument support mechanism for establishing stable support for dental instruments such as a dental cutting tool, a drill, a fiber scope and a diamond bar within an oral cavity in desired positions therein to perform a dental treatment or test.

BACKGROUND OF THE INVENTION

In performing a dental treatment such as dental test or dental operation, a dentist and his/her assistant must use various types of dental instruments. Such dental instruments include grinding tools such as a diamond bar for grinding a tooth, and cutting tools such as a dental reamer or a dental file for forming a root canal. Further, for an implant such as an artificial root of tooth, a hole must be created on a bone in the jaw, which requires a special drill.

Further, in the dental treatment, since the object in the oral cavity is not easily visible, a special tool such as a fiber scope has to be used in the location near the object to observe the object through the monitor. Moreover, a drain pipe may also be used to remove the fluid such as saliva and or debris in the oral cavity.

Ordinarily, such dental instruments, i.e., a diamond bar, reamer, and file for drilling and cutting, a fiber scope for monitoring, and a drain pipe for cleaning the oral cavity, have to be supported by the hands of the dentist and/or dentist's assistant. Thus, in a typical example of dental treatment, the fiber scope and the drain pipe are held by, for example, the assistant while the diamond bar and/or reamer are operated by the dentist.

However, this process of performing the dental treatment while holding the dental instruments in the hands requires a high level of skill and experience by both the dentist and the assistant. Because the oral cavity is small, it is difficult to hold the various instruments in the right positions in the oral cavity. Further, since the small movement of the fiber scope is magnified in the microscope monitor, the manual handling of the fiber scope needs special talents and experience.

SUMMARY OF THE INVENTION

This invention has been made to solve the problems involved in the dental treatment and operation in the conventional technology. It is, therefore, an object of the present invention to provide a dental instrument support mechanism which can stably support dental instruments with a relatively simple structure.

It is another object of the present invention to provide a dental instrument support mechanism which can stably support dental instruments while maintaining the positional relationship with the object.

It is a further object of the present invention to provide a dental instrument support mechanism which is able to adjust the positions and directions of the dental instrument held at the end of the support mechanism.

In the present invention, the dental instruments support mechanism is comprised of a base portion, and a support arm connected to the base portion at one end for holding a dental instrument at another end. The dental instrument held by the support arm is fixedly maintained a positional relationship with dental object in an oral cavity of a patient. The dental instrument support mechanism is attached to one or more of a head, face, jaw, tooth of the patient or a treatment bed.

Each component of the dental instrument support mechanism is provided with sufficient stiffness to endure loads received during movements of dental instrument or dental treatment using the dental instrument wherein a distance and an angle of the dental instrument relative to the dental object in the oral cavity is adjustable.

Preferably, the dental instrument on the support arm is moveable along a predetermine route in the oral cavity. A plurality of dental instruments can be supported by the dental instrument support mechanism. Alternatively, two or more dental instrument support mechanisms support one dental instrument in the oral cavity of the patient.

Preferably, the support arm has a column connected to the base portion and an arm connected to the column at one end for mounting the dental instrument at another end, wherein the arm is moveable along the column. To achieve this, a combination of a pinion gear and a rack gear are incorporated in the support arm.

According to the present invention, the dental instrument support mechanism has the base portion and the support arm attached to the base portion at one end to support the dental instrument at the other end. The dental instrument supported by the support arm can be fixedly maintained in the oral cavity with a constant positional relationship with the intended object. Therefore, the dental instruments can be fixed in the desired positions and orientation in the oral cavity without requiring any experience of skill by the user, thereby enabling the dental treatment with high efficiency and accuracy.

BRIEF DESCRIPTION OF THE DRAWINGS

FIG. 1 shows a dental instrument support mechanism in the first embodiment of the present invention where

FIG. 3 is a diagram showing another example of the base portion of the dental instrument support mechanism of the present invention which is designed to be fitted with the tooth wherein

FIG. 4 shows a dental instrument support mechanism in the second embodiment of the present invention where

DETAILED DESCRIPTION OF THE PREFERRED EMBODIMENTS

Figure 1A:
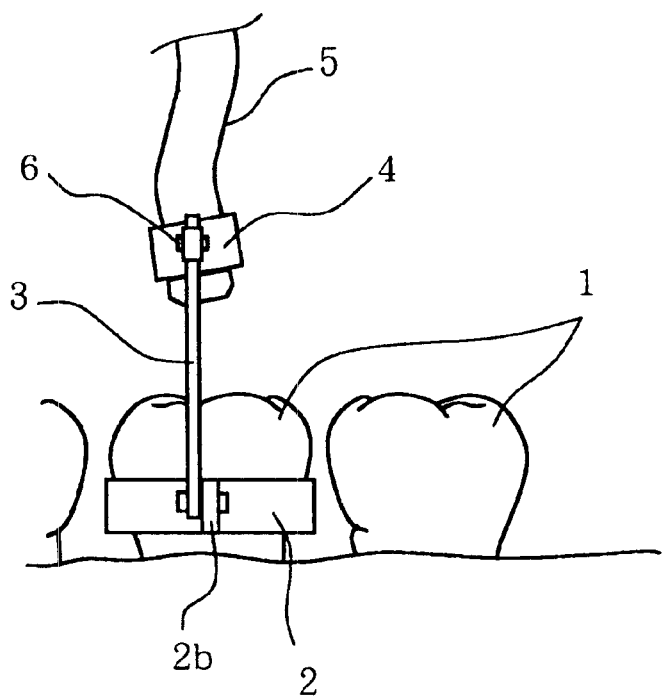
FIG. 1(a) is a front view showing the actual use thereof in the oral cavity.
Figure 1C:
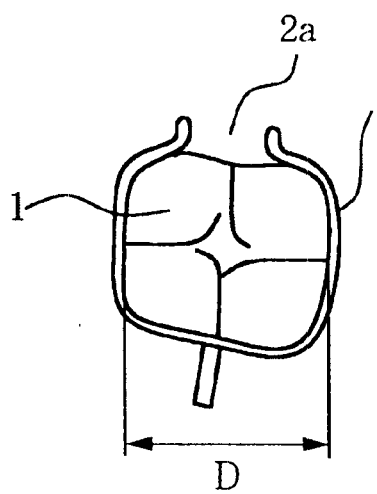
FIG. 1(c) is a top view where the base portion thereof is fitted with the tooth.
Figure 1B:
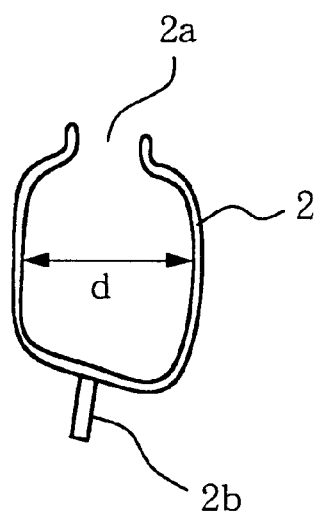
FIG. 1(b) is a top view of the base portion thereof.

The dental instrument support mechanism of the present invention will be described in detail with reference to the accompanying drawings wherein like numerals refer to like parts throughout. FIGS. 1(a)–1(c) show a first embodiment of a dental instrument support mechanism of the present invention where FIG. 1(a) is a front view thereof showing the actual use in the oral cavity, FIG. 1(b) is a top view of the base portion of the support mechanism, and FIG. 1(c) is a top view where the base portion thereof is fitted with the tooth.

In FIG. 1, numeral 1 indicates teeth in an oral cavity, and numeral 2 indicates a base portion of the dental instrument support mechanism. As shown in FIG. 1(b), the base portion 2 is made of a belt like material which is curved to form a C-shape and has an opening 2a at its end. The belt like material is preferably made of metal, in particular stainless steel, although other kinds of material such as plastic can also be used.

A projection 2b is attached to the base portion 2 by welding, for example, as shown in FIGS. 1(a) and 1(b) to attach one end of a support arm 3 thereto. The other end of the support arm 3 is above the teeth 1 to hold a dental instrument 4. In this example, the dental instrument 4 is a fiber scope. Numeral 5 indicates a fiber cable connected to the dental instrument 4, i.e., the fiber scope.

In the above example, the dental instrument 4 is mounted, in a close proximate with the target tooth, at the top end of the support arm 3, on a base plate 6. Preferably, the base plate 6 has a structure similar to a universal head of a camera so that the fiber scope can be oriented in any desired directions. As a consequence, the position of the dental instrument 4 can be freely adjusted relative to the object in the oral cavity and can be fixed to the desired position by fastening a screw or the like.

Other than the fiber scope, the dental instrument 4 can be a microscope or a magnifier which requires fine adjustment and fixation of a focal point thereof. A light which is ordinarily built on a dental chair can be inserted in the oral cavity and held by the support mechanism of the present invention. In this situation, because the light only illuminates the inside of the oral cavity, the patient is not dazzled by the light and the dentist needs not to worry about his/her shade. Further, by fixing the drain pipe with use of the dental instrument support mechanism, the oral cavity can be kept clean throughout the dental treatment without the help by the assistant.

The dental instrument 4 includes a cutting tool such as a dental reamer or a dental file, and a grinding tool such as a diamond bar and a drill, thus, involving mechanical vibrations. Thus, the base portion 2, the projection 2b and the support arm 3 are preferably configured so as to be free from any deformation or displacement by the reaction to the use of such dental instruments.

For this purpose, the connection point such as between the base portion 2 and the support arm 3, and between the support arm 3 and the dental instrument 4, is configured by using a combination of a dovetail groove and a dovetail key, a coupling structure by a square shaped projection and a square shaped recess, a coupling structure using a doweled pin, and the like. By forming the connection point in the manner noted above, the position of the connection point can be securely maintained while achieving a desired stiffness of the dental instrument support mechanism. Further improvement in the stiffness of the dental instrument support mechanism is available by using I-shaped, L-shaped or U-shaped material in cross section or tubular material for each component of the dental instrument support mechanism.

As shown in FIG. 1(b), the base portion 2, in its free situation, has a width d which is smaller than that of the tooth 1. When mounted on the tooth 1, by inserting in the gaps between the teeth in the manner shown in FIGS. 1(a) and 1(c), the width d of the base portion 2 is enlarged to the width D, thereby being firmly and elastically attached to the tooth. The top view of FIG. 1(c) does not show the support arm 3 or the dental instrument 4 for the simplicity of illustration.

In the foregoing embodiment, the dental instrument 4 on the support arm 3 is intended to treat the tooth on which the base portion 2 is mounted. However, the dental instrument 4 can be held by the support mechanism of the present invention to treat or study the tooth next or two or more teeth next to the one being attached to the base portion 2 by modifying the shape of the support arm 3 to be suitable for such use. In other words, the support mechanism can hold the dental instrument 4 to perform a dental treatment for the position having no teeth, such as forming an artificial tooth.

By mounting the fiber scope as the dental instrument 4, it becomes possible to easily monitor the location of the tooth which is not easily observable by the naked eyes, such as a root canal. In such an occasion, in the prior art, the fiber scope is manually held in which small movements are magnified, and thus causing the monitor display difficult to see. In the present invention, however, the positional relationship between the fiber scope and the location of the object is always the same, resulting in an easily observable image on the monitor.

In the present invention, two or more dental instrument support mechanisms are used in the oral cavity of the patient at the same time to support two or more dental instruments. Such two or more dental instrument support mechanisms can also be used to support one dental instrument such as, for example, a one which is highly sensitive to a mechanical vibration or shock and the like.

Figure 2:
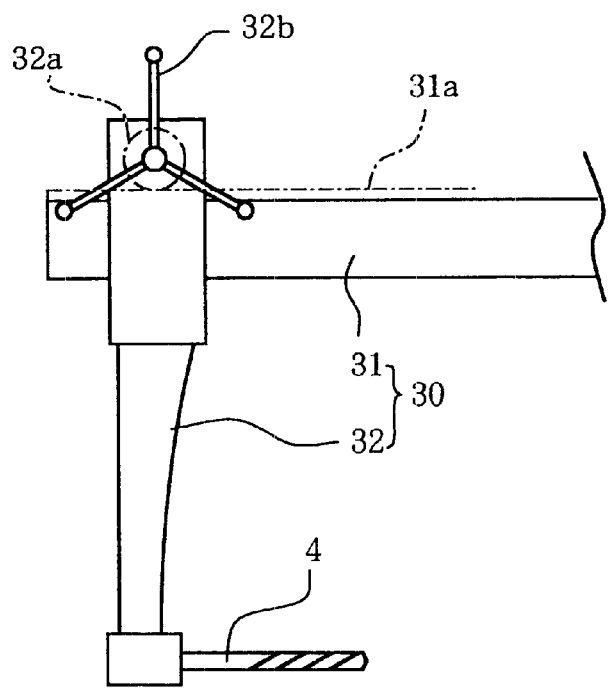
FIG. 2 is a diagram showing another example of the support portion of the dental instrument support mechanism of the present invention having pinion and rack gears.

FIG. 2 shows another example of the support arm in the dental instrument support mechanism of the present invention. A support arm 30 of FIG. 2 has a column 31 connected to the base portion 2, and an arm 32 connected almost perpendicularly to the column 31. At the connection of the column 31 and the arm 32, there is provided with a pinion gear 32a which is freely rotatable and is engaged with a rack gear 31a formed on the column 31. The pinion gear 32a has a handle 32b on its shaft.

Thus, by rotating the handle 32b, the dental instrument 4 such as a dental file can be moved in a direction parallel with the column 31. This arrangement is effective in accurately producing a hole on the tooth. By further incorporating the base plate 6 of FIG. 1 which is a universal base plate, the column 31 can be inclined in any desired directions, making it possible that the dental instrument 4 moves to any positions with any directions to perform the dental treatment. Further, a brake may be provided to the handle 32b to control the rotation, thereby being able to fixedly stop the dental instrument at any desired locations.

Figure 3A:
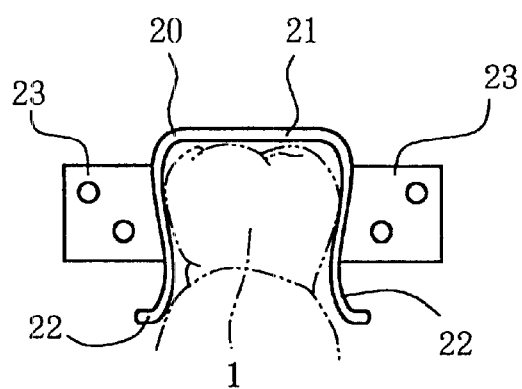
FIG. 3(a) is a side view.
Figure 3B:
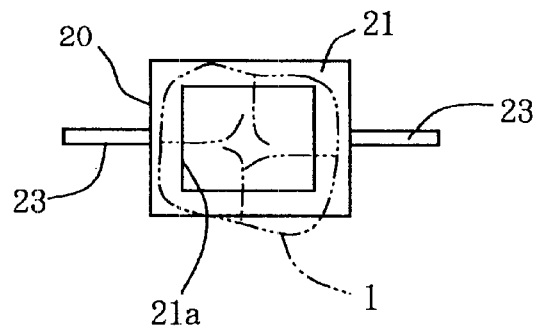
FIG. 3(b) is a top view of the base portion.

Another example of the base portion 2 of the dental instrument support mechanism is shown in FIG. 3. In this example, a base portion 20 has a cap like shape to cover the tooth 1 when mounting the support mechanism on the tooth. The base portion 20 has a main body 21, elastic pieces 22 integrally formed with the main body 21 to pressingly sandwich the tooth 1. At the top of the main body, an opening 21a is formed to ensure an enough space for the treatment of the tooth.

Similar to the example of FIG. 1, the base portion 20 has, at both sides, a pair of projections 23 integrally formed thereon for mounting the support arm. In this example, since the projections 23 for mounting the support arm are provided at both sides of the tooth, the dental instrument can be held in more stable manner. Alternatively, two support arms are attached to the base portion 20 via the projections 23 to support two or more dental instruments on the dental instrument support mechanism.

Figure 4A:
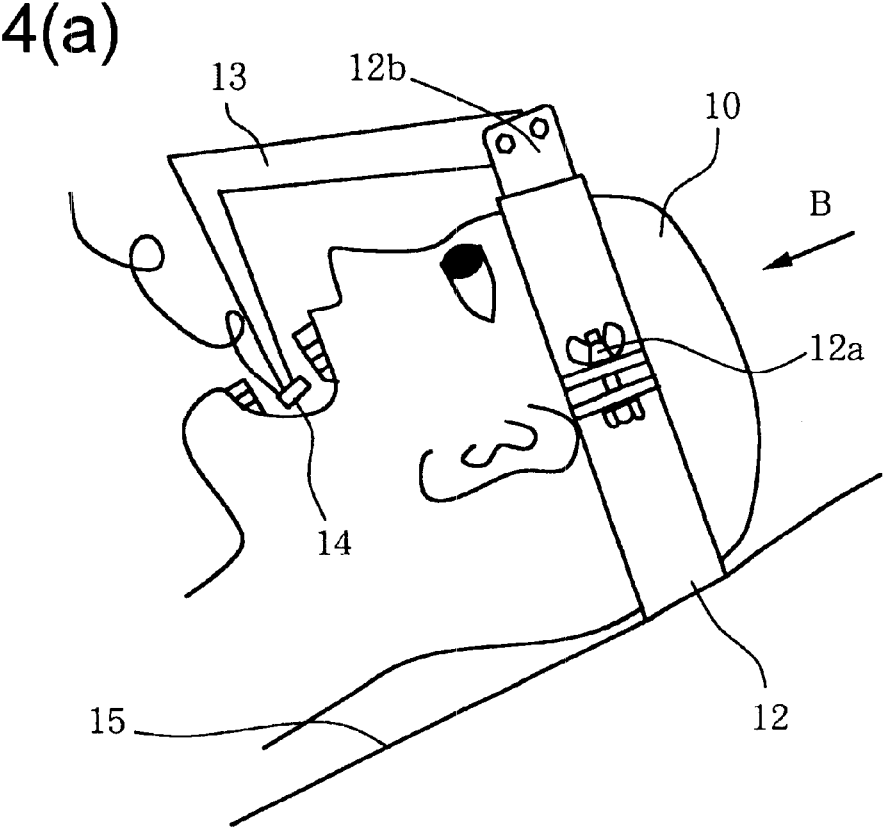
FIG. 4(a) is a side view thereof showing the actual use.
Figure 4B:
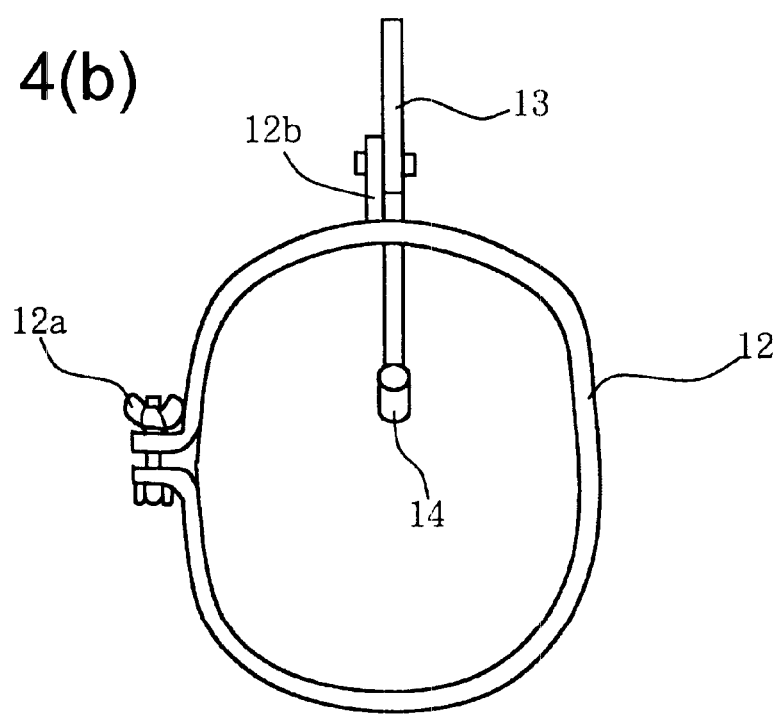
FIG. 4(b) is a diagram of the second embodiment viewed from the direction indicated by the arrow B of FIG. 4(a).

FIG. 4 shows a dental instrument support mechanism in the second embodiment of the present invention. In this example, a base portion 12 of the dental instrument support mechanism is attached to the head 10 of the patient. Namely, the base portion 12 is put on the head 10 in a manner of using a headband and is tightened on the head 10 by fastening a wing nut 12a. The base portion 12 has a projection 12b which is attached thereto by welding, for example, to connect a support arm 13. The support arm 13 in this example has an L-shape to hold the dental instrument at the end. Similar to the first embodiment described above, the connection point between the support arm 13 and the dental instrument 14, and the cross sectional structure of the support arm 13 are so configured that the support mechanism is free from any deformation or displacement and has sufficient mechanical stiffness.

In this embodiment, the dental instrument 14 supported by the arm 13 can maintain the desired position relative to the oral cavity. However, since the positional reference in this embodiment is the head 10 of the patient, various positions on the upper jaw of the patient are constant while the positions on the lower jaw are not constant. Thus, the embodiment of FIG. 4 is suitable for the dental treatment concerning the upper jaw of the patient.

In the embodiment of FIG. 4, by incorporating the universal base plate 6 of FIG. 1 and the pinion and rack gears of FIG. 2, the dental instrument 14 can freely move along the support arm 13 and the angle of the dental instrument can be freely adjusted in the oral cavity. After adjusting the position and angle, such position and angle are fixed by tightening the screws and the like. Thus, the dental instrument support mechanism of the present invention can position the dental instrument in the oral cavity and maintain the position or move the dental instrument along the predetermined route in the oral cavity.

The embodiment of FIG. 4 is possible to have the base portion 12 and the support arm 13 which are substantially larger than that in the embodiment of FIGS. 1 and 2. Thus, by having the pinion and rack gears to move the dental instrument back and forth, a relatively large sized dental instrument for a heavy duty can also be used. Accordingly, the dental instrument support mechanism of the present invention can be used for the dental treatment which requires a relatively large force such as drilling a hole in the jaw for forming an artificial tooth.

In the example described above with reference to FIG. 4, although the base portion 12 is fixed to the head 10 of the patient, it is also possible to attach the base portion 12 to the face of the patient or to both the head and the face of the patient. Further, in the above mentioned embodiments, the base portion is fixed to the head or tooth in the manner grasping the same. However, other ways of fixing the base portion are also possible, for example, by using a bridge rod between the teeth such as in the right and left and forming the support arm and other components on the bridge rod. A further example is an indentation formed on the bed 15 so that the head of the patient is placed on the indentation, which can define the position of the oral cavity of the patient so that the base portion can be mounted on the bed 15. Furthermore, the base portion can be attached to the lower jaw of the patient so that the positional relationship between the dental instrument and the object in the oral cavity in the lower jaw can be maintained constant. Thus, even when the dental treatment is conducted using the microscope, there is no need to adjust the focal point, because the relative distance is kept constant.

As has been described, according to the present invention, the dental instrument support mechanism has the base portion and the support arm attached to the base portion at one end to support the dental instrument at the other end. The dental instrument supported by the support arm can be fixedly maintained in the oral cavity with a constant positional relationship with the intended object. Therefore, the dental instruments can be fixed in the desired positions and orientation in the oral cavity without requiring any experience of skill, thereby enabling the dental treatment with high efficiency and accuracy.

Although only a preferred embodiment is specifically illustrated and described herein, it will be appreciated that many modifications and variations of the present invention are possible in light of the above teachings and within the purview of the appended claims without departing the spirit and intended scope of the invention.

What is claimed is:

1. A dental instrument support mechanism, comprising:

a base portion;

a support arm connected to the base portion at one end for holding a dental instrument at another end;

wherein the dental instrument held by the support arm is fixedly maintained a positional relationship with a dental object in an oral cavity of a patient, and wherein the base portion is elastically formed and inwardly presses the tooth from sides thereof when being attached to the tooth.

2. A dental instrument support mechanism as defined in claim 1, wherein the base portion is attached to one or more of a head, face, jaw, tooth of the patient or a treatment bed.

3. A dental instrument support mechanism as defined in claim 1, wherein each component of the support mechanism is provided with sufficient stiffness to endure loads received during movements of dental instrument or dental treatment using the dental instrument.

4. A dental instrument support mechanism as defined in claim 1, wherein a plurality of dental instruments can be supported by the dental instrument support mechanism.

5. A dental instrument support mechanism as defined in claim 1, wherein two or more dental instrument support mechanisms support one dental instrument in the oral cavity of the patient.

6. A dental instrument support mechanism as defined in claim 1, wherein the base portion has a cap like shape to cover the tooth to be attached and elastic pieces which inwardly press the tooth from sides thereof when being attached to the tooth.

7. A dental instrument support mechanism as defined in claim 1, wherein the base portion is attached to a treatment bed so that the dental instrument supported by the dental instrument support mechanism is maintained a predetermined positional relationship relative to the treatment bed.

8. A dental instrument support mechanism as defined in claim 1, wherein the base portion has a projection through which the support arm is attached thereto.

9. A dental instrument support mechanism as defined in claim 1, wherein the base portion has two or more projections through which two or more support arms are attached thereto.

10. A dental instrument support mechanism as defined in claim 1, wherein the support arm has a column connected to the base portion and an arm connected to the column at one end for mounting the dental instrument at another end, wherein the arm is moveable along the column.

11. A dental instrument support mechanism as defined in claim 10, wherein a combination of a pinion gear and a rack gear is provided to the support arm, thereby moving the arm in parallel with the column.

12. A dental instrument support mechanism as defined in claim 1, wherein the dental instrument is mounted on the another end of the support arm through a base plate whose angle is freely adjustable by a structure of a universal head provided to the base plate.

13. A dental instrument support mechanism as defined in claim 6, wherein the base portion has a hole at a top thereof to ensure an opening for treatment of the tooth when the base portion covers the tooth.

* * * * *